(12) United States Patent
Themelis

(10) Patent No.: US 11,494,954 B2
(45) Date of Patent: Nov. 8, 2022

(54) OPTICAL SYSTEM AND CORRESPONDING APPARATUS, METHOD AND COMPUTER PROGRAM

(71) Applicant: LEICA INSTRUMENTS (SINGAPORE) PTE. LTD., Singapore (SG)

(72) Inventor: George Themelis, Lindau (DE)

(73) Assignee: LEICA INSTRUMENTS (SINGAPORE) PTE. LTD., Singapore (SG)

( * ) Notice: Subject to any disclaimer, the term of this patent is extended or adjusted under 35 U.S.C. 154(b) by 28 days.

(21) Appl. No.: 17/087,664

(22) Filed: Nov. 3, 2020

(65) Prior Publication Data

US 2021/0142533 A1 May 13, 2021

(30) Foreign Application Priority Data

Nov. 8, 2019 (EP) ..................................... 19208053

(51) Int. Cl.
*G06T 11/00* (2006.01)
*A61B 90/30* (2016.01)
(Continued)

(52) U.S. Cl.
CPC ............ *G06T 11/001* (2013.01); *A61B 90/30* (2016.02); *A61B 90/361* (2016.02);
(Continued)

(58) Field of Classification Search
CPC combination set(s) only.
See application file for complete search history.

(56) References Cited

U.S. PATENT DOCUMENTS

| 2013/0114043 A1* | 5/2013 | Balan | H04N 13/383 |
| | | | 351/210 |
| 2018/0088323 A1* | 3/2018 | Bao | G02B 27/017 |

(Continued)

FOREIGN PATENT DOCUMENTS

| JP | 2017146598 A | 8/2017 |
| JP | 2021090753 A | 6/2021 |

(Continued)

*Primary Examiner* — Wesner Sajous
(74) *Attorney, Agent, or Firm* — 2SPL Patent Attorneys PartG mbB; Kieran O'Leary

(57) ABSTRACT

Examples relate to an optical system and to a corresponding apparatus, method and computer program. The optical system comprises a display module for providing a visual overlay to be overlaid over an object in an augmented reality or mixed reality environment. The optical system comprises at least one sensor for sensing at least one optical property of the object. The optical system comprises a processing module configured to determine the at least one optical property of the object using the at least one sensor. The processing module is configured to determine a visual contrast between the visual overlay to be overlaid over the object and the object, as perceived within a field of view of the augmented reality or mixed reality environment, based on the at least one optical property of the object. The processing module is configured to selectively adjust an illumination of one of more portions of the field of view, or an optical attenuation of the one of more portions of the field of view, based on the determined visual contrast between the visual overlay to be overlaid over the object and the object.

15 Claims, 3 Drawing Sheets

(51) Int. Cl.
*G06T 7/90* (2017.01)
*G02B 27/01* (2006.01)
*G06T 5/00* (2006.01)
*G06T 7/00* (2017.01)
*H04N 5/445* (2011.01)
*H04N 5/57* (2006.01)
*A61B 90/00* (2016.01)

(52) U.S. Cl.
CPC .......... *G02B 27/0101* (2013.01); *G06T 5/007* (2013.01); *G06T 7/0012* (2013.01); *G06T 7/90* (2017.01); *A61B 2090/365* (2016.02); *A61B 2090/373* (2016.02); *G02B 2027/014* (2013.01); *G02B 2027/0118* (2013.01); *G02B 2027/0138* (2013.01); *G06T 2207/10024* (2013.01); *G06T 2207/30004* (2013.01)

(56) References Cited

U.S. PATENT DOCUMENTS

| | | | |
|---|---|---|---|
| 2018/0204361 A1* | 7/2018 | Tinsman | G06T 11/60 |
| 2019/0025590 A1* | 1/2019 | Haddick | G02B 27/14 |
| 2020/0211273 A1* | 7/2020 | Kass | G06T 19/006 |
| 2021/0349535 A1* | 11/2021 | Border | G02B 27/0093 |
| 2022/0012877 A1* | 1/2022 | Buckler | G06T 7/10 |
| 2022/0139014 A1* | 5/2022 | Tinsman | G06T 19/20 |
| | | | 345/633 |

FOREIGN PATENT DOCUMENTS

| | | |
|---|---|---|
| WO | 2018057050 A1 | 3/2018 |
| WO | 2018063528 A1 | 4/2018 |
| WO | 2019071157 A1 | 4/2019 |

* cited by examiner

OPTICAL SYSTEM AND CORRESPONDING APPARATUS, METHOD AND COMPUTER PROGRAM

CROSS REFERENCE TO RELATED APPLICATIONS

This application claims priority of European patent application number 19208053.9 filed Nov. 8, 2019, the entire disclosure of which is incorporated by reference herein.

TECHNICAL FIELD

Examples relate to an optical system and to a corresponding apparatus, method and computer program.

BACKGROUND

Augmented Reality (AR) and Merged Reality are topics in research and development. In augmented reality, objects of a real-world environment are overlaid with computer-generated information, e.g. in order to provide contextual information on the objects of the real-world environment. For example, in an operating room, augmented reality may be used by a surgeon to view additional information about the tissue the surgery is performed on, e.g. to highlight pathologic tissue during surgery. In merged reality (i.e. mixed reality), the real world and a virtual world are merged/mixed, such that the objects of both worlds can interact. Both technologies are often implemented using semi-transparent mirrors and projection devices, or partially transparent displays. Augmented and merged reality visualization technologies often suffer from color distortion due to technological limitations in image mixing and overlay. For example, holographic glasses may physically overlay digital images on the field of view of the natural vision. This process may result in low contrast for bright objects, such as well illuminated brain tissue.

SUMMARY

There may be a desire for an improved concept for an augmented or merged reality environment.

This desire is addressed by the subject-matter of the independent claims.

Embodiments are based on the finding that a brightness of a real object that is perceived in an AR/MR environment can be altered to improve a contrast between a visual overlay that is to be overlaid over the object and the perception of the object. This can be done selectively, e.g. in order to avoid decreasing a brightness of surrounding objections or surrounding portions of the object. In general, there are at least two general concepts for altering the perception of the real object: by selectively altering the illumination of the object, or by selectively attenuating the perception of the object. For example, the illumination of the object, or the observation of the illumination of the object, may be spatially adjusted, e.g. spatially attenuated. This may lead to an improved contrast between the overlay and the object in the AR/MR environment.

Embodiments of the present disclosure provide an optical system. The optical system comprises a display module for providing a visual overlay to be overlaid over an object in an augmented reality or mixed reality environment. The optical system comprises at least one sensor for sensing at least one optical property of the object. The optical system comprises a processing module configured to determine the at least one optical property of the object using the at least one sensor. The processing module is configured to determine a visual contrast between the visual overlay to be overlaid over the object and the object, as perceived within a field of view of the augmented reality or mixed reality environment, based on the at least one optical property of the object. The processing module is configured to selectively adjust an illumination of one of more portions of the field of view, or an optical attenuation of the one of more portions of the field of view, based on the determined visual contrast between the visual overlay to be overlaid over the object and the object. This may provide an improved contrast between the one of more portions of the field of view and the visual overlay.

In at least some embodiments, the sensor module comprises a camera. The processing module may be configured to obtain a camera image of the object using the camera. The processing module may be configured to determine a visual representation of the object, as perceived within the augmented reality or mixed reality environment, using the camera image. The processing module may be configured to determine the visual contrast based on the visual overlay and based on the camera image. The determined visual contrast may be used to determine whether a selective adjustment of the illumination or the optical attenuation is required for a portion of the object.

For example, the at least one optical property of the object may comprise a brightness of the one or more portions of the field of view. The processing module may be configured to selectively adjust the brightness of the one or more portions of the field of view, as perceived within the augmented reality or mixed reality environment, by selectively adjusting the illumination or the optical attenuation of the one or more portions of the field of view. For example, the illumination or attenuation may be adjusted such that the one or more portions of the field of view are perceived at a reduced brightness, increasing a contrast between the visual overlay and the respective one or more portions.

Additionally or alternatively, a color composition of the object may be considered. For example, the at least one optical property of the object may comprise a color composition of the object. The processing module may be configured to selectively adjust the illumination or the optical attenuation of the one or more portions of the field of view based on the color composition of the object. For example, an adjustment might only be desired at a portion of the object if a contrast between a color of the visual overlay and a color of the portion of the field of view is low.

In at least some embodiments, the processing module is configured to selectively adjust the illumination or the optical attenuation of the one or more portions of the field of view based on a visual contrast between the color composition of the object at the one or more portions of the field of view and a color composition of the visual overlay at a position corresponding to the object. For example, the adjustment may be performed such that the visual contrast is increased between the color composition of the one or more portions of the field of view and the color composition of the visual overlay at a position corresponding to the object.

For example, the processing module may be configured to selectively adjust a spectral characteristic of the one or more portions of the field of view, as perceived within the augmented reality or mixed reality environment, by selectively adjusting a spectral characteristic of the illumination or a spectral characteristic of the optical attenuation of the one or more portions of the field of view. This may lead to a color shift, or selective attenuation, of the one or more portions of the field of view, improving a contrast between the one or more portions of the field of view and the visual overlay.

In at least some embodiments, the optical system comprises an illumination source for illuminating the field of view. The processing module may be configured to control the illumination source in order to selectively adjust the illumination of the one or more portions of the field of view. The illumination source may be under control of the processing module, and may thus implement the adjustment of the selective illumination of the one or more portions of the field of view.

For example, the processing module may be configured to control the illumination source such that the illumination source is configured to provide an illumination of the one or more portions of the field of view that is different from an illumination of adjacent portions of the field of view. For example, the processing module may be configured to control the illumination source such that at least one of a light intensity and a spectral characteristic of the illumination is different between the illumination of the one or more portions of the field of view and the illumination of adjacent portions of the field of view. This may provide the selective adjustment of the illumination.

In some embodiments, the optical system comprises an optical attenuation module arranged within a light path of the optical system. The processing module may be configured to control the optical attenuation module such that the optical attenuation module is configured to provide an attenuation of light emanating from, or incident to, the one or more portions of the field of view being different from an attenuation of light emanating from, or incident to, adjacent portions of the field of view, thereby selectively adjusting the optical attenuation of the one or more portions of the field of view. For example, the processing module may be configured to control the optical attenuation module such that at least one of an intensity of the optical attenuation and a spectral characteristic of the optical attenuation is different between the optical attenuation of light emanating from, or incident to, the one or more portions of the field of view and the optical attenuation of light emanating from, or incident to, adjacent portions of the field of view. This may provide the selective adjustment of the optical attenuation.

For example, the optical attenuation module may be arranged to be within a light path between an illumination source of the optical system and the object. This may provide an optical attenuation of the illumination of the object before the illumination reaches the object, resulting in a selective adjustment of the illumination of the one of more portions of the field of view. Alternatively or additionally, the optical attenuation module may be arranged to be within a light path between a user of the optical system and the object. This may provide a selective optical attenuation of the one of more portions of the field of view.

In at least some embodiments, the processing module is configured to selectively adjust the illumination of the one of more portions of the field of view, or the optical attenuation of the one of more portions of the field of view, in order to achieve at least a pre-defined contrast between the visual overlay and the object. The pre-defined contrast may increase a legibility, or perceivability of the visual overlay.

For example, the visual overlay may be overlaid over the object using a semitransparent mirror of the optical system. For example, the overlay may be projected onto the semitransparent mirror. The object may be seen through the semitransparent mirror, resulting in an AR/MR experience without a lag in the perception of the object.

In some embodiments, the object is a sample of organic tissue. The sample of organic tissue may be overlaid with contextual information, e.g. information on healthy or pathologic tissue, or information about features hidden behind a surface of the organic tissue.

For example, the visual overlay may be configured to highlight the one or more portions of the sample of organic tissue. The highlighted one or more portions may be used to guide a surgeon during surgery, for example.

For example, the optical system may be a microscope, e.g. a surgical microscope. The optical system may thus be used to aid a surgeon during surgery.

Alternatively, the optical system may be an endoscope. When used with an endoscope, a camera image may often suffer from high reflections due to a close proximity between the light source and the camera. Embodiments may be used to selectively adjust the illumination or attenuation, in order to provide a sufficient contrast between the visual overlay and the camera image. Furthermore, the image recorded by the camera may be improved, as overexposure of the one or more portions of the field of view may be avoided.

Embodiments of the present disclosure further provide a corresponding apparatus for an optical system. The apparatus comprises an interface for communicating with one or more components of the optical system. The apparatus comprises a processing module configured to determine at least one optical property of an object using at least one sensor of the optical system. The processing module is configured to determine a visual contrast, as perceived within a field of view of an augmented reality or mixed reality environment, between a visual overlay to be overlaid over the object in the augmented reality or mixed reality environment and the object, based on the at least one optical property of the object. The processing module is configured to selectively adjust an illumination of one of more portions of the field of view, or an optical attenuation of the one of more portions of the field of view, based on the determined visual contrast between the visual overlay to be overlaid over the object and the object.

Embodiments of the present disclosure further provide a corresponding method for an optical system. The method comprises determining at least one optical property of an object using at least one sensor of the optical system. The method comprises determining a visual contrast, as perceived within a field of view of an augmented reality or mixed reality environment, between a visual overlay to be overlaid over the object in the augmented reality or mixed reality environment and the object, based on the at least one optical property of the object. The method comprises selectively adjusting an illumination of one of more portions of the field of view, or an optical attenuation of the one of more portions of the field of view, based on the determined visual contrast between the visual overlay to be overlaid over the object and the object. Embodiments of the present disclosure further provide a computer program with a program code for performing the method when the computer program is executed on a processor.

BRIEF DESCRIPTION OF THE DRAWING VIEWS

Some examples of apparatuses and/or methods will be described in the following by way of example only, and with reference to the accompanying figures, in which FIGS. 1a to 1c show block diagrams of embodiments of an optical system and of an apparatus for an optical system;

DETAILED DESCRIPTION

Various examples will now be described more fully with reference to the accompanying drawings in which some examples are illustrated. In the figures, the thicknesses of lines, layers and/or regions may be exaggerated for clarity.

Accordingly, while further examples are capable of various modifications and alternative forms, some particular examples thereof are shown in the figures and will subsequently be described in detail. However, this detailed description does not limit further examples to the particular forms described. Further examples may cover all modifications, equivalents, and alternatives falling within the scope of the disclosure. Same or like numbers refer to like or similar elements throughout the description of the figures, which may be implemented identically or in modified form when compared to one another while providing for the same or a similar functionality.

It will be understood that when an element is referred to as being "connected" or "coupled" to another element, the elements may be directly connected or coupled or via one or more intervening elements. If two elements A and B are combined using an "or", this is to be understood to disclose all possible combinations, i.e. only A, only B as well as A and B, if not explicitly or implicitly defined otherwise. An alternative wording for the same combinations is "at least one of A and B" or "A and/or B". The same applies, mutatis mutandis, for combinations of more than two Elements.

The terminology used herein for the purpose of describing particular examples is not intended to be limiting for further examples. Whenever a singular form such as "a," "an" and "the" is used and using only a single element is neither explicitly or implicitly defined as being mandatory, further examples may also use plural elements to implement the same functionality. Likewise, when a functionality is subsequently described as being implemented using multiple elements, further examples may implement the same functionality using a single element or processing entity. It will be further understood that the terms "comprises," "comprising," "includes" and/or "including," when used, specify the presence of the stated features, integers, steps, operations, processes, acts, elements and/or components, but do not preclude the presence or addition of one or more other features, integers, steps, operations, processes, acts, elements, components and/or any group thereof.

Unless otherwise defined, all terms (including technical and scientific terms) are used herein in their ordinary meaning of the art to which the examples belong.

Figure 1A:
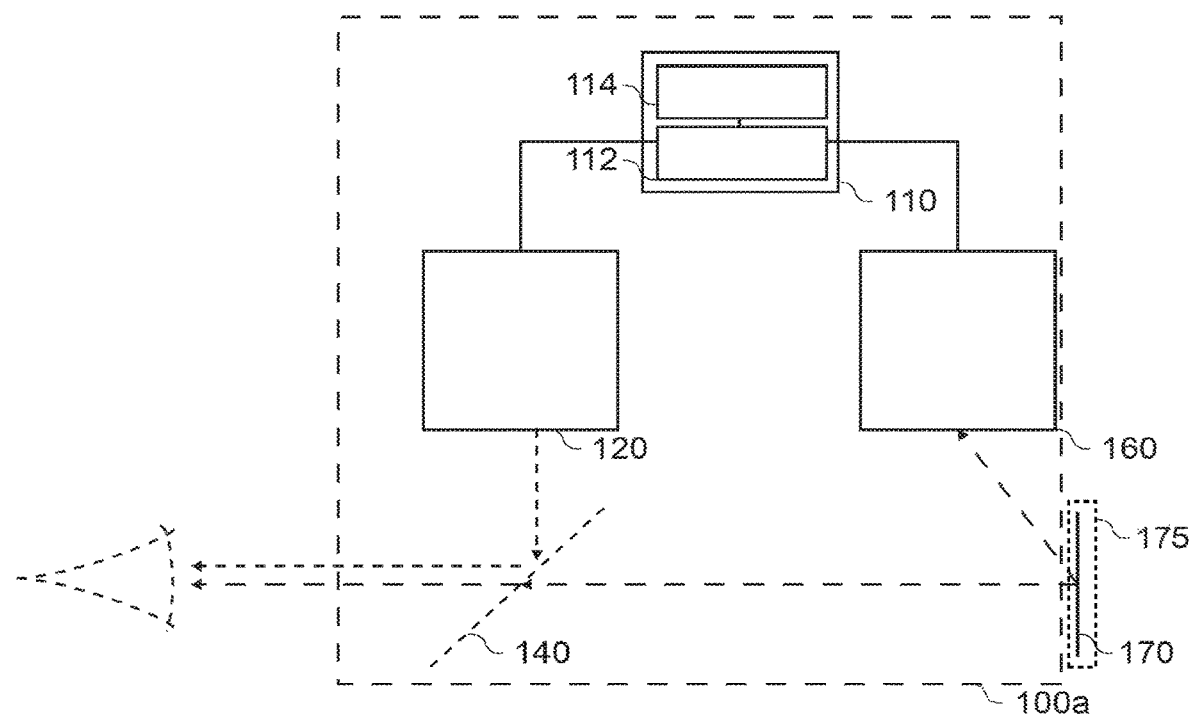
Figure 1B:
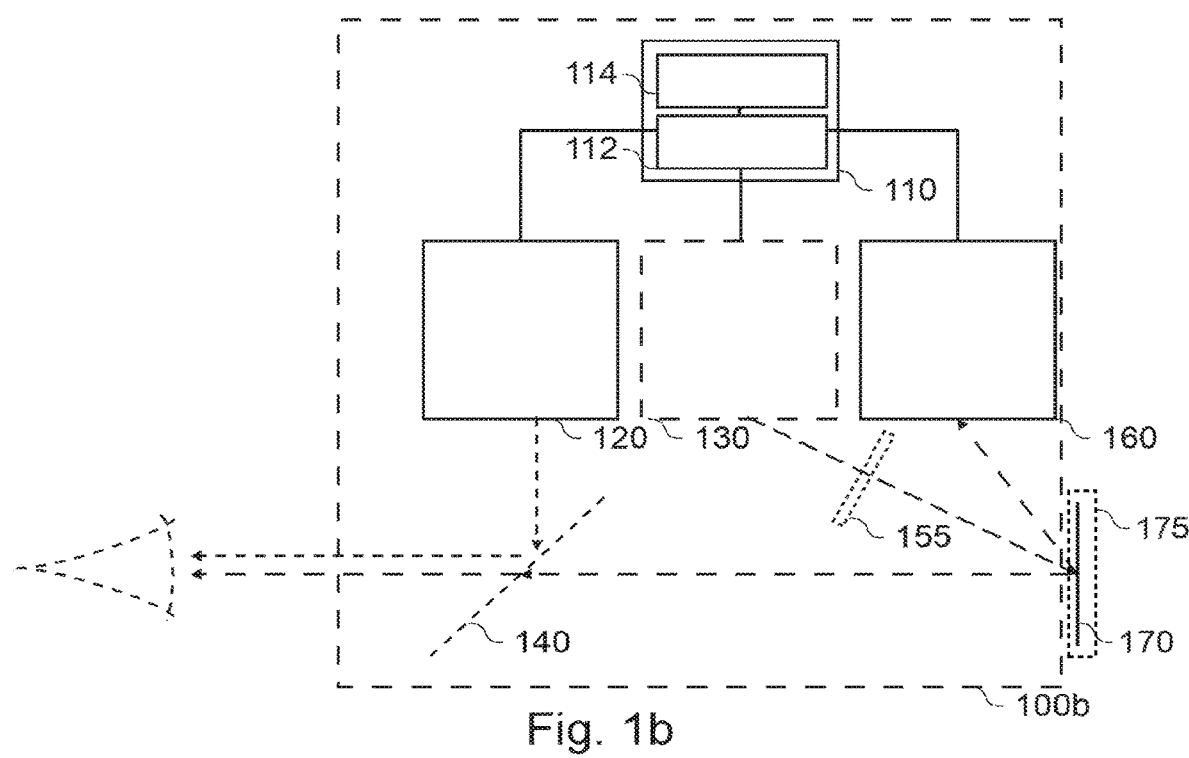
Figure 1C:
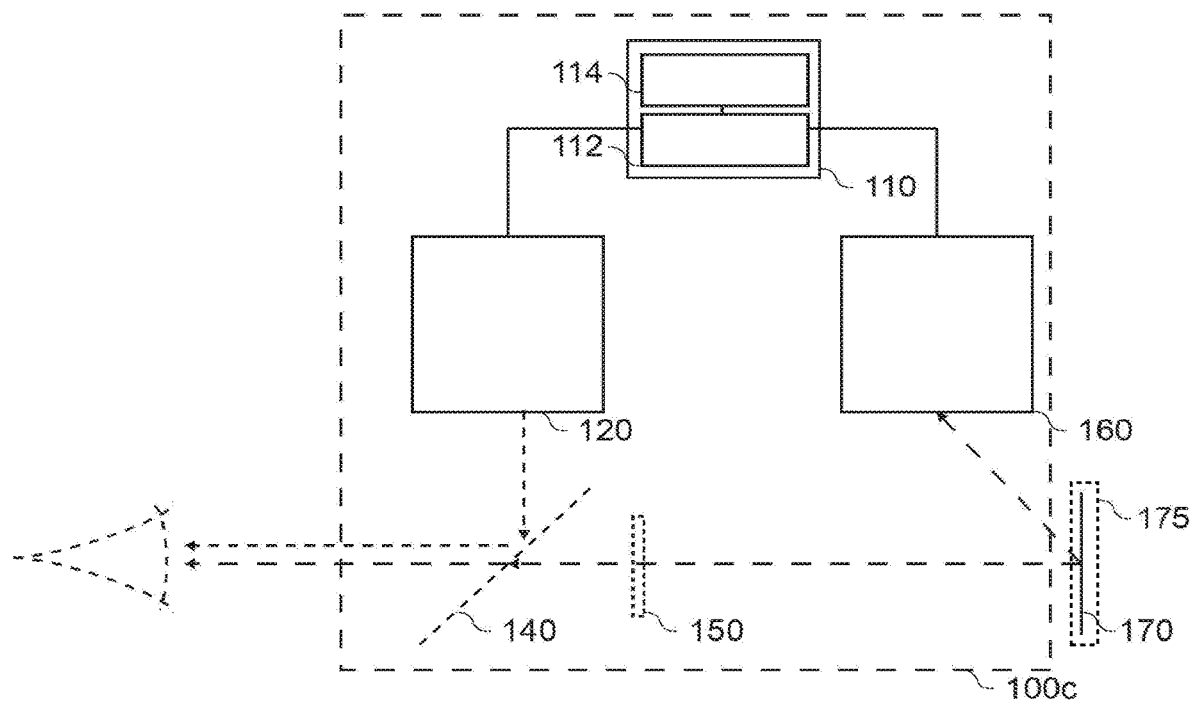

FIGS. 1a to 1c show block diagrams of embodiments of an optical system 100a; 100b; 100c. The optical system comprises a display module 120 for providing a visual overlay to be overlaid over an object 170 in an augmented reality or mixed reality environment. The optical system comprises at least one sensor 160 for sensing at least one optical property of the object 170. The optical system comprises a processing module 114, which is coupled to the display module 120 and the at least one sensor 160, e.g. via an interface 112. FIGS. 1a to 1c further shows an apparatus 110 for the optical system, comprising the interface 112 and the processing module 114. For example, the apparatus may be suitable for controlling the optical system, e.g. the apparatus 110 may be a control apparatus of the optical system. The processing module 114 is configured to determine the at least one optical property of the object 170 using the at least one sensor 160. The processing module is configured to determine a visual contrast between the visual overlay to be overlaid over the object 170 and the object, as perceived within a field of view of the augmented reality or mixed reality environment, based on the at least one optical property of the object 170. The processing module is configured to selectively adjust an illumination of one of more portions of the field of view, or an optical attenuation of the one of more portions of the field of view, based on the determined visual contrast between the visual overlay to be overlaid over the object 170 and the object 170. In FIGS. 1a to 1c, a semi-transparent mirror 140 is used to overlay the visual overlay over the object. In other words, the visual overlay may be overlaid over the object 170 using a semi-transparent mirror 140 of the optical system. Alternative approaches, such as translucent displays, may be used instead.

Embodiments of the present disclosure relate to an optical system and to a corresponding apparatus, method and computer program. The optical system may be considered an Augmented Reality (AR) or a Merged/Mixed Reality (MR)-System, i.e. a system, in which a computer-generated visual overlay is overlaid over a real object (i.e. an object from the real world that is not generated by a computer). The optical system may be configured to provide the augmented reality or mixed reality environment, which may be an environment wherein computer-generated elements (i.e. the visual overlay) and real objects are both visible, and in which the computer-generated elements are overlaid over the real objects, e.g. to provide auxiliary or contextual information on the real objects. Such an optical system may, for example, be used in a surgical setting. For example, during surgery, the optical system may be used to display auxiliary or contextual information for the surgeon. For example, a camera (such as the at least one sensor 160) may be used to perform fluorescence imaging, e.g. to obtain images that show a fluorescence of a fluorescent dye that has been injected into pathologic tissue. The location of the pathologic tissue may be extracted based on the obtained image, and overlaid over the object (i.e. the pathologic tissue) by the optical system. Accordingly, the object 170 may be a sample of organic tissue, e.g. a sample of organic tissue of a surgical site. The visual overlay may be configured to highlight the one or more portions of the sample of organic tissue, or of any sample, e.g. by providing a color overlay for the one or more portions and/or by providing one or more lines indicating the extent of the one or more portions. For example, the one or more portions of the sample of organic tissue may comprise (or be) one or more pathologic portions (or at least "suspicious" portions) of the sample of organic tissue. Alternatively or additionally, the one or more portions of the sample of organic tissue may comprise (or be) blood vessels (e.g. arteries and veins), which may be highlighted in contrasting colors (e.g. red for arteries, blue for veins). Alternatively or additionally, the one or more portions of the sample of organic tissue may comprise (or be) one or more portions of the sample of organic tissue that the surgery is to be performed on.

For example, in a surgical or research environment, the optical system may be a microscope, e.g. a surgical microscope, an endoscope or an image-guided system. Image guided systems are routinely used as an add-on to surgical microscopes to assist surgeons navigate within the tissue volume, and reach pathologic tissue areas, while avoiding hurting sensitive but vital structures such as brain and vessels. Image guided systems are utilizing pre-operative three-dimensional scans of the patient, such as MRI (Magnetic Resonance Imaging) scans and X-ray angiography scans. For example, the one or more portions of the sample of organic tissue may be overlaid with an image generated from a pre-operative three-dimensional scan of the patient. Apart from the surgical field, the optical system may be a wearable optical device, such as AR/MR glasses, or a mobile device, such as a smartphone or a tablet computer.

The processing module is configured to determine the at least one optical property of the object 170 using the at least one sensor. In at least some embodiments, the at least one property of the object 170 may be "as perceived" by the user, e.g. under the assumption that the illumination or optical attenuation of the object is not changed. The at least one optical property of the object may relate to how the object is perceived within the field of view. The at least one property of the object 170 may change as the illumination or attenuation is adjusted. For example, as the illumination or attenuation is adjusted, a perceived brightness of the one or more portions of the object may change. The processing module 114 may compensate internally for these changes, e.g. by including a compensation factor that takes into account the adjustments performed. Alternatively, the at least one property of the object 170 may be independent of the adjustment of the attenuation (albeit dependent on the adjustment of the illumination, as the illumination may also be perceived by the at least one sensor). The processing module may be configured to map the at least one optical property of the object (e.g. sensor data of the at least one sensor) onto the field of view, e.g. using a two-dimensional projection of the at least one optical property of the object onto the field of view, and map the at least one optical property of the object to the perception of the object within the optical system. Correspondingly, the object may be mapped onto the field of view. For example, the one or more portions of the field of view may be mapped to one or more corresponding portions of the object. The visual overlay may be aligned with the mapping of the object within the field of view.

In at least some embodiments, the at least one optical property of the object may relate at least to the one or more portions of the field of view and the corresponding one or more portions of the object, as these are the portions of the object being changed. There are multiple optical properties that may be considered when examining the visual contrast between the object and the overlay. For example, the at least one optical property of the object 170 may comprise a brightness of the one or more portions of the field of view. Accordingly, the at least one sensor 160 may comprise a brightness sensor that is configured to determine a brightness of the one or more portions of the field of view and of the corresponding one or more portions of the object. Additionally or alternatively, the at least one optical property of the object 170 may comprise a color composition of the object 170 (e.g. of the one or more portions of the field of view). For example, the color composition of the object 170 may indicate one or more colors of the object, as perceived within the optical imaging system. For example, the at least one optical property of the object 170 may comprise a color composition of the one or more portions of the field of view, which are, in turn, based on the color of the one or more corresponding portions of the object. Accordingly, the at least one sensor 160 may comprise a spectral analysis sensor that is configured to determine a color composition of the object. Instead of (or as) the brightness sensor and the spectral analysis sensor, a camera may be used to determine the respective information. For example, the sensor module 160 may comprise a camera. The processing module 114 may be configured to obtain a camera image of the object using the camera. The processing module 114 may be further configured to determine the at least one optical property of the object, e.g. the brightness of the one or more portions of the field of view and/or the color composition of the object or of the field of view, based on the camera image, e.g. using image analysis.

In at least some embodiments, the at least one sensor may perceive the object similar to a user of the optical system. For example, the at least one sensor may be arranged such that it perceives the optical attenuation of the one or more portions of the field of view. Alternatively, the at least one sensor may be arranged such that it does not perceive the optical attenuation of the one or more portions of the field of view, e.g. as the optical attenuation is not performed for light incident to the at least one sensor. In general, the at least one sensor may be arranged such that it directly faces the object as shown in FIGS. 1*a* to 1*c*. Alternatively, the at least one sensor may be configured to sense the at least one optical property of the object via at least one optical element that redirects the light incident from the object. For example, the optical system may comprise a further semitransparent mirror, and the at least one sensor may be configured to observe the object via the further semitransparent mirror.

The processing module is configured to determine the visual contrast between the visual overlay to be overlaid over the object 170 and the object, as perceived within the field of view of the augmented reality or mixed reality environment, based on the at least one optical property of the object 170. In the context of the present disclosure, the term "as perceived within the field of view of the augmented reality or mixed reality environment" is used. In general, the term is used to cover a variety of embodiments, as there are a variety of approaches that can be used to change a perception of an object. For example, light that is emitted towards the object may be adjusted, either by an illumination source or by an optical attenuation module. Alternatively or additionally, light that is emanating from the object can be adjusted, e.g. using an optical attenuation module. These different concepts are united by the concept of the "perception within the field of view of the augmented reality or mixed reality environment". In effect, the "perception within the field of view of the augmented reality or mixed reality environment" denotes the object, as it is perceived by the user, including the adjustments that have been performed by the illumination source or the optical attenuation module(s). For example, as laid out above, the processing module 114 may be configured to map sensor data (e.g. a camera image) of the at least one sensor 160, and therefore the at last one optical property of the object, onto the field of view. Additionally, the processing module 114 may be configured to map the visual overlay onto the field of view. Based on these two mappings, the processing module 114 may determine the visual contrast between the object as mapped into the field of view and of the visual overlay as mapped into the field of view. In other words, the processing module 114 may be configured to determine the visual contrast between the visual overlay to be overlaid over the object 170 and the object, as perceived within the field of view of the augmented reality or mixed reality environment, based on the at last one optical property of the object, as mapped onto the field of view, and based on the visual overlay, as mapped onto the field of view. For example, the processing module 114 may be configured to determine a visual representation of the object, as perceived within the augmented reality or mixed reality environment, using the sensor data of the at least one sensor, e.g. using the camera image, and to determine the visual contrast based on the visual overlay and based on the camera image.

In at least some embodiments, the visual contrast comprises at least one of two components: a brightness contrast and a color contrast. In other words, the processing module may be configured to determine a contrast between the brightness of the visual overlay to be overlaid over the object 170 and a brightness the object, as perceived within the field of view of the augmented reality or mixed reality environment. Additionally or alternatively, the processing module may be configured to determine a contrast between the color of the visual overlay to be overlaid over the object 170 and a color the object, as perceived within the field of view of the augmented reality or mixed reality environment. If one of the components is not large enough, e.g. if a difference between the brightness of the visual overlay and of the object, as perceived within the field of view of the augmented reality or mixed reality environment or a difference between the color of the visual overlay and of the object, as perceived within the field of view of the augmented reality or mixed reality environment, is not large enough, the illumination of the object or the optical attenuation of the field of view may be selectively adjusted. For example, the processing module 114 may be configured to selectively adjust the illumination of the one of more portions of the field of view, or the optical attenuation of the one of more portions of the field of view, in order to achieve at least a pre-defined contrast between the visual overlay and the object 170.

In embodiments, the adjustment of the illumination and/or of the optical attenuation is selective, e.g. spatially selective. In other words, the illumination and/or the optical attenuation may be merely adjusted for the one or more portions of the field of view, and not for the entire field of view. The illumination and/or the optical attenuation of the one or more portions may be adjusted such that the illumination and/or the optical attenuation is different between the one or more portions of the field of view and adjacent portions of the field of view. For example, the one or more portions of the field of view may be one or more portions that are overlaid with the visual overlay. Additionally, there may be other portions of the field of view that are also overlaid with the visual overlay, and which require no adjustment of the illumination or of the optical attenuation. Accordingly, the processing module 114 may be configured to determine the one or more portions of the field of view that require an adjustment of the illumination or of the optical attenuation. In other words, the processing module 114 may be configured to select the one or more portions of the field of view based on visual contrast between the visual overlay to be overlaid over the object 170 and the object 170. For example, if the visual contrast is too low at a portion of the field of view, the respective portion may be selected for one or more portions of the field of view.

In at least some embodiments, the processing module is configured to selectively adjust the illumination of the one or more portions of the field of view. This may be achieved twofold—by controlling an illumination source, and/or by controlling an optical attenuation module that is arranged between an illumination source and the object. Both concepts may be used to adjust a brightness and a spectral characteristic of the one or more portions.

For example, the brightness one of the one or more portions of the field of view may be selectively adjusted. In other words, the processing module 114 may be configured to selectively adjust the brightness of the one or more portions of the field of view, as perceived within the augmented reality or mixed reality environment, by selectively adjusting the illumination or the optical attenuation of the one or more portions of the field of view. For example, the illumination or attenuation may be adjusted such that the one or more portions of the field of view are perceived at a reduced brightness, increasing a contrast between the visual overlay and the respective one or more portions.

In some embodiments, as shown in FIG. 1*b*, the optical system may comprise an illumination source 130, which may be coupled with the processing module 114, e.g. via the interface 112. In some embodiments, the illumination source may be suitable for, or configured to, provide a uniform light. For example, the illumination source may be a Light Emitting Diode-based illumination source. In this case, the selective adjustment may be performed via one or more optical attenuation modules. Alternatively, the light source may be suitable for, or configured to, providing/provide a non-uniform light. For example, the illumination source may be configured to provide light having a spatially adjustable brightness. Additionally or alternatively, the illumination source may be configured to provide light having spatially adjustable spectral characteristics. Both traits may, for example, be implemented using an imaging projector. In other words, the illumination source may be an imaging projector, which may be configured to provide a light having a spatially non-uniform brightness and/or a spatially non-uniform spectral characteristic. In some embodiments, the imaging projector may be multispectral projector configured to provide a light having a spatially non-uniform brightness and/or a spatially non-uniform spectral characteristic using different images for different spectral bands.

The processing module 114 may be configured to control the illumination source 130 in order to selectively adjust the illumination of the one or more portions of the field of view, e.g. such that the illumination of the object at the one or more portions of the field of view has a brightness or spectral characteristic that is different from adjacent portions of the object. In other words, the processing module 114 may be configured to control the illumination source 130 such that the illumination source 130 is configured to provide an illumination of the one or more portions of the field of view 1'75 that is different from an illumination of adjacent portions of the field of view. For example, the processing module 114 may be configured to control the illumination source 130 such that a light intensity of the illumination is different between the illumination of the one or more portions of the field of view (i.e. of the. corresponding one or more corresponding portions of the object) and the illumination of adjacent portions of the field of view or of adjacent portions of the object.

Alternatively, the light intensity of the illumination may be selectively changed using an optical attenuation module 155 being arranged between the illumination source 130 and the object 170 (see FIG. 1*b*). The optical attenuation module 155 and, likewise, attenuation modules 140 and/or 150), may be coupled to the processing module 114, e.g. via the interface 112. In other words, the optical system may comprise an optical attenuation module 155 that is arranged to be within a light path between an illumination source (e.g. the illumination source 130) of the optical system 100*b* and the object 170. In other words, the processing module 114 may be configured to control the optical attenuation module 155 such that the optical attenuation module 155 is configured to provide an attenuation of light incident to the one or more portions of the field of view being different from an attenuation of light incident to adjacent portions of the field of view, thereby selectively adjusting the optical attenuation of the one or more portions of the field of view. For example, the processing module 114 may be configured to control the optical attenuation module 155 such that at least one of an intensity of the optical attenuation and a spectral characteristic of the optical attenuation is different between the optical attenuation of light incident to the one or more portions of the field of view and the optical attenuation of light incident to adjacent portions of the field of view. This may be achieved using a partially transparent display, such as a Liquid Chrystal Display having no backlight, an Organic Light Emitting Diode (OLED) display, or a DLP (Digital Light Processing) module as attenuation module 155. Such a display may be used to selectively adjust the brightness or the spectral characteristic of the illumination.

The processing module 114 may be configured to control the optical attenuation module 155 such that a light intensity of the illumination is different between the illumination of the one or more portions of the field of view and the illumination of adjacent portions of the field of view. In other words, the processing module 114 may be configured to use the optical attenuation module 155 to selectively attenuate the light that is incident to the object, in order to selectively adjust the light intensity of the light that is incident to the object.

Alternatively or additionally, the spectral characteristic of the illumination may be selectively adjusted, e.g. based on the color composition of the object. In general, the spectral characteristic of the illumination may refer to the "color of the light" of the illumination. In other words, a color of the illumination may be (spatially) selectively adjusted. The processing module 114 may be configured to selectively adjust the illumination of the one or more portions of the field of view based on the color composition of the object 170. For example, for colors of the object that do not provide sufficient contrast for the visual overlay, the illumination may be changed such that the color is shifted towards a color that provides more contrast for the visual overlay. The adjustment may be performed such that the visual contrast is increased between the color composition of the one or more portions of the field of view and the color composition of the visual overlay at a position corresponding to the object. In other words, the processing module 114 may be configured to selectively adjust the illumination of the one or more portions of the field of view based on a visual contrast between the color composition of the object at the one or more portions of the field of view 175 and a color composition of the visual overlay at a position corresponding to the object 170. As laid out above, the processing module may be configured to select the one or more portions based on the visual contrast between the color composition of the object at the one or more portions of the field of view 175 and a color composition of the visual overlay at a position corresponding to the object 170. Subsequently, the illumination (or optical attenuation) of the one or more portions of the field of view may be selectively adjusted.

The processing module 114 may be configured to selectively adjust the spectral characteristic of the one or more portions of the field of view, as perceived within the augmented reality or mixed reality environment, by selectively adjusting the spectral characteristic of the illumination of the one or more portions of the field of view. Again, the adjustment being selective means that the adjustment is performed differently for the one or more portions than for adjacent portions of the field of view or object.

In some embodiments, the illumination may be adjusted by controlling the illumination source. In other words, the processing module 114 may be configured to control the illumination source 130 such that the spectral characteristic of the illumination is different between the illumination of the one or more portions of the field of view and the illumination of adjacent portions of the field of view. Alternatively, the illumination may be adjusted by controlling the optical attenuation module. The spectral characteristic of the illumination may be changed using the optical attenuation module 155 being arranged between the illumination source 130 and the object 170 (see FIG. 1b). In other words, the processing module 114 may be configured to control the optical attenuation module 155 such that the spectral characteristic of the illumination is different between the illumination of the one or more portions of the field of view and the illumination of adjacent portions of the field of view.

Alternatively, the brightness or spectral characteristic of the one or more portions of the field of view may be adjusted by adjusting the perception (within the augmented reality or mixed reality environment) of the light that is emanating from the object. For example, as shown in FIG. 1c, the optical system may comprise an optical attenuation module 140; 150 that is arranged within a light path of the optical system 100a; 100c. In this case, the optical attenuation module 140; 150 may be arranged to be within a light path between a user of the optical system 100a; 100c and the object 170. For example, the optical attenuation module 140; 150 may be a partially transparent display. In some embodiments, the optical attenuation module 150 may, as shown in FIG. 1c, be separate from the semitransparent mirror 140. Alternatively, the semitransparent mirror 140 may include or function as optical attenuation module. For example, the semi-transparent mirror may be coupled with a partially transparent display. The optical attenuation module can be used to selectively adjust a brightness or a spectral characteristic, as perceived within the augmented reality or mixed reality environment. Accordingly, the processing module 114 may be configured to control the optical attenuation module 140; 150 such that the optical attenuation module 140; 150 is configured to provide an attenuation of light emanating from the one or more portions of the field of view being different from an attenuation of light emanating from adjacent portions of the field of view, thereby selectively adjusting the optical attenuation of the one or more portions of the field of view. The processing module 114 may be configured to control the optical attenuation module 140; 150 such that at least one of the intensity of the optical attenuation and the spectral characteristic of the optical attenuation is different between the optical attenuation of light emanating from the one or more portions of the field of view and the optical attenuation of light emanating from, adjacent portions of the field of view.

For example, the processing module 114 may be configured to selectively adjust the brightness of the one or more portions of the field of view, as perceived within the augmented reality or mixed reality environment, by selectively adjusting the optical attenuation of the one or more portions of the field of view, e.g. using the optical attenuation module 140; 150.

Additionally or alternatively, the processing module 114 may be configured to selectively adjust the optical attenuation of the one or more portions of the field of view based on a visual contrast between the color composition of the object at the one or more portions of the field of view 175 and a color composition of the visual overlay at a position corresponding to the object 170, e.g. similar to the adjustment of the illumination. For example, for colors of the object that do not provide sufficient contrast for the visual overlay, the optical attenuation may be changed such that the color is shifted towards a color that provides more contrast for the visual overlay. As laid out above, the processing module may be configured to select the one or more portions based on the visual contrast between the color composition of the object at the one or more portions of the field of view 175 and a color composition of the visual overlay at a position corresponding to the object 170. Subsequently, the optical attenuation of the one or more portions of the field of view may be selectively adjusted. For example, the processing module 114 may be configured to selectively adjust the spectral characteristic of the one or more portions of the field of view, as perceived within the augmented reality or mixed reality environment, by selectively adjusting the spectral characteristic of the optical attenuation of the one or more portions of the field of view, e.g. using the optical attenuation module 140; 150. In other words, the processing module may be configured to shift the color of the one or more portions of the field of view by selectively attenuating the one or more portions of the field of view, e.g. in order to increase the contrast between the one or more portions of the field of view and the visual overlay. Again, the adjustment of the attenuation is selective, e.g. different between the one or more portions of the field of view and adjacent portions of the field of view. In this context, the spectral characteristic of the of the one or more portions of the field of view, as perceived within the augmented reality or mixed reality environment, may refer to the "color" of the one or more portions of the field of view, as they are perceived by the user of the optical system. This color may be shifted in order to increase the optical contrast between the perception of the object and the visual overlay.

The optical system comprises a display module 120 for providing the visual overlay to be overlaid over an object 170 in the augmented reality or mixed reality environment. In some embodiments, the display module 120 may comprise a projector, to project the visual overlay towards the user via the semitransparent mirror 140. Such as setup is shown in FIGS. 1a to 1c. Alternatively, the display module 120 may comprise a partially transparent display that is arranged within a light path between the object and the user.

The interface 112 may correspond to one or more inputs and/or outputs for receiving and/or transmitting information, which may be in digital (bit) values according to a specified code, within a module, between modules or between modules of different entities. For example, the interface 12 may comprise interface circuitry configured to receive and/or transmit information. In embodiments the processing module 114 may be implemented using one or more processing units, one or more processing devices, any means for processing, such as a processor, a computer or a programmable hardware component being operable with accordingly adapted software. In other words, the described function of the processing module 114 may as well be implemented in software, which is then executed on one or more programmable hardware components. Such hardware components may comprise a general purpose processor, a Digital Signal Processor (DSP), a micro-controller, etc.

More details and aspects of the optical system or the apparatus for the optical system are mentioned in connection with the proposed concept or one or more examples described above or below (e.g. FIG. 2 or 3). The optical system or the apparatus for the optical system may comprise one or more additional optional features corresponding to one or more aspects of the proposed concept or one or more examples described above or below.

Figure 2:
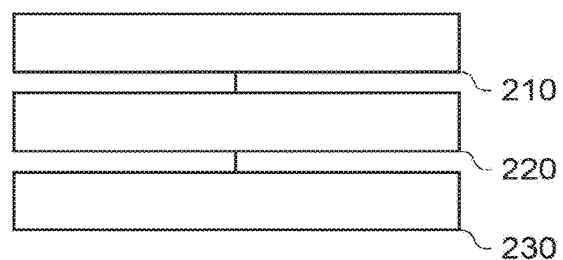
FIG. 2 shows a flow chart of an embodiment of method for an optical system.

FIG. 2 shows a flow chart of a (corresponding) method for an optical system. For example, the optical system may be implemented similar to the optical system of FIG. 1a, 1b or 1c. The method comprises determining 210 at least one optical property of an object using at least one sensor of the optical system. The method comprises determining 220 a visual contrast, as perceived within a field of view of an augmented reality or mixed reality environment, between a visual overlay to be overlaid over the object in the augmented reality or mixed reality environment and the object, based on the at least one optical property of the object. The method further comprises selectively adjusting 230 an illumination of one of more portions of the field of view, or an optical attenuation of the one of more portions of the field of view, based on the determined visual contrast between the visual overlay to be overlaid over the object and the object.

As indicated above, features described in connection with the optical system of FIGS. 1a to 1c may be likewise applied to the method of FIG. 2.

More details and aspects of the method are mentioned in connection with the proposed concept or one or more examples described above or below (e.g. FIG. 1 or 3). The method may comprise one or more additional optional features corresponding to one or more aspects of the proposed concept or one or more examples described above or below.

Embodiments of the present disclosure may provide automatic color and/or contrast considering a background image (i.e. the object) in AR/MR. Embodiments may thus provide an improved AR image.

Figure 3:
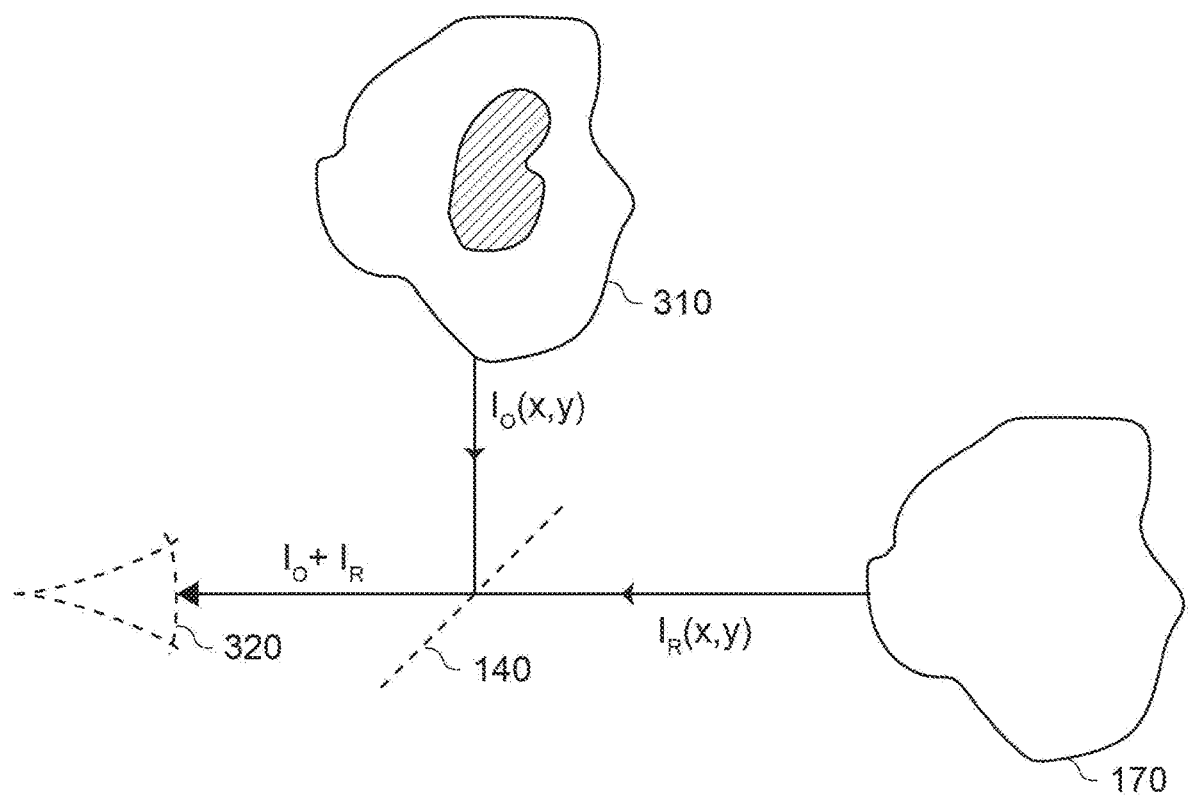
FIG. 3 shows a schematic overview of a perception of an object in an AR/MR environment.

AR/MR reality devices may project images to the eye which superimpose to the naturally observed images of objects (see FIG. 3). FIG. 3 shows a schematic overview of a perception of an object 170 in an AR/MR environment. In a simplistic model, it may be assumed that the naturally observed image of an object 170 (as observed by a user 320) can be described as a spatial distribution of light $I_R(x,y)$, typically reflected light, and the overlaid image 310 can be written similarly as $I_O(x,y)$. A properly aligned semitransparent mirror 140 allows the user to observe a composite image which comprises (or consists of) of the algebraic addition of the two images: $I=I_O+I_R$. When $I_R$ is relatively weak compared to $I_O$, then $I_O$ can be observed with the intended contrast/quality. However, when $I_R$ is much brighter than $I_O$, then $I_O$ might be observed in very low contrast, or not observable at all. An example of the deterioration of the observed contrast is when the system intents to label an object with vivid green color, while the object is white. Ideally, the overlay area should be seen as green, i.e. high G (Green) value, but very low R (Red) and B (Blue) values. However, due to the fact that the object is already white, the R, G, and B values might anyway be high. Therefore, the system might only create greenish-whites but not green impressions on white objects.

In order to increase the perceived contrast of the overlay image, the light intensity of the observed object may be attenuated. This can be achieved in two different ways. For example, illumination attenuation may be used to attenuate the intensity of illumination. This may facilitate an implementation, but might not always be feasible, unless the illumination (e.g. the illumination source 130) is controllable (e.g. endoscopes, microscopes). Alternatively or additionally, observation attenuation may be used to attenuate the transmission of the mirror (or similarly attenuate the observable light intensity if the technology used is not a simple mirror). This approach can be technically more challenging, but may be used in any illumination conditions.

The optical attenuation of both approaches listed above can be spectrally and spatially uniform, e.g. using a neutral density filter which attenuates all wavelengths and areas in the same way. An alternative approach that is used in at least some embodiments may be to create a spectrally and spatially variable attenuation. The technical solution may be different for the two attenuation ways. For illumination attenuation, an imaging projector may be used instead of a conventional light source. In other words, the illumination source may be an imaging projector. This concept could extend the RGB concept into a multispectral projector which could create different images for multiple spectral bands. For observation attenuation, a spatial light modulator such as an LCD or DLP placed on an image-forming point of the imaging axis may be used (same principle as projectors).

More details and aspects of the concept are mentioned in connection with the proposed concept or one or more examples described above or below (e.g. FIG. 1a to 2). The concept may comprise one or more additional optional features corresponding to one or more aspects of the proposed concept or one or more examples described above or below.

As used herein the term "and/or" includes any and all combinations of one or more of the associated listed items and may be abbreviated as "/".

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus. Some or all of the method steps may be executed by (or using) a hardware apparatus, like for example, a processor, a microprocessor, a programmable computer or an electronic circuit. In some embodiments, some one or more of the most important method steps may be executed by such an apparatus.

Depending on certain implementation requirements, embodiments of the invention can be implemented in hardware or in software. The implementation can be performed using a non-transitory storage medium such as a digital storage medium, for example a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may, for example, be stored on a machine readable carrier.

Other embodiments comprise the computer program for performing one of the methods described herein, stored on a machine readable carrier.

In other words, an embodiment of the present invention is, therefore, a computer program having a program code for performing one of the methods described herein, when the computer program runs on a computer.

A further embodiment of the present invention is, therefore, a storage medium (or a data carrier, or a computer-readable medium) comprising, stored thereon, the computer program for performing one of the methods described herein when it is performed by a processor. The data carrier, the digital storage medium or the recorded medium are typically tangible and/or non-transitionary. A further embodiment of the present invention is an apparatus as described herein comprising a processor and the storage medium.

A further embodiment of the invention is, therefore, a data stream or a sequence of signals representing the computer program for performing one of the methods described herein. The data stream or the sequence of signals may, for example, be configured to be transferred via a data communication connection, for example, via the internet.

A further embodiment comprises a processing means, for example, a computer or a programmable logic device, configured to, or adapted to, perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

LIST OF REFERENCE SIGNS

100a Optical system
100b Optical system
100c Optical system
110 Apparatus
112 Interface
114 Processing module
120 Display module
130 Illumination source
140 Semitransparent mirror
150 Attenuation module
155 Attenuation module
160 Sensor
170 Object
175 Field of view portion
210 Determining at least one optical property
220 Determining a visual contrast
230 Selectively adjust an illumination or optical attenuation
310 Visual overlay
320 Perception of user

What is claimed is:

1. An optical system comprising:
a display module for providing a visual overlay to be overlaid over an object in an augmented reality or mixed reality environment;
at least one sensor for sensing at least one optical property of the object; and
a processing module configured to:
determine the at least one optical property of the object using the at least one sensor,
determine a visual contrast between the visual overlay to be overlaid over the object and the object, as perceived within a field of view of the augmented reality or mixed reality environment, based on the at least one optical property of the object, and
selectively adjust an illumination of one of more portions of the field of view, or an optical attenuation of the one of more portions of the field of view, based on the determined visual contrast between the visual overlay to be overlaid over the object and the object.

2. The optical system according to claim 1, wherein the sensor module comprises a camera, wherein the processing module is configured to obtain a camera image of the object using the camera, wherein the processing module is configured to determine a visual representation of the object, as perceived within the augmented reality or mixed reality environment, using the camera image, and to determine the visual contrast based on the visual overlay and based on the camera image.

3. The optical system according to claim 1, wherein the at least one optical property of the object comprises a brightness of the one or more portions of the field of view, wherein the processing module is configured to selectively adjust the brightness of the one or more portions of the field of view, as perceived within the augmented reality or mixed reality environment, by selectively adjusting the illumination or the optical attenuation of the one or more portions of the field of view.

4. The optical system according to claim 1, wherein the at least one optical property of the object comprises a color composition of the object, wherein the processing module is configured to selectively adjust the illumination or the optical attenuation of the one or more portions of the field of view based on the color composition of the object.

5. The optical system according to claim 4, wherein the processing module is configured to selectively adjust the illumination or the optical attenuation of the one or more portions of the field of view based on a visual contrast between the color composition of the object at the one or more portions of the field of view and a color composition of the visual overlay at a position corresponding to the object.

6. The optical system according to claim 1, wherein the processing module is configured to selectively adjust a spectral characteristic of the one or more portions of the field of view, as perceived within the augmented reality or mixed reality environment, by selectively adjusting a spectral characteristic of the illumination or a spectral characteristic of the optical attenuation of the one or more portions of the field of view.

7. The optical system according to claim 1, further comprising an illumination source for illuminating the field of view, wherein the processing module is configured to control the illumination source in order to selectively adjust the illumination of the one or more portions of the field of view.

8. The optical system according to claim 7, wherein the processing module is configured to control the illumination source such that the illumination source is configured to provide an illumination of the one or more portions of the field of view that is different from an illumination of adjacent portions of the field of view.

9. The optical system according to claim 1, further comprising an optical attenuation module arranged within a light path of the optical system, wherein the processing module is configured to control the optical attenuation module such that the optical attenuation module provides an attenuation of light emanating from, or incident to, the one or more portions of the field of view being different from an attenuation of light emanating from, or incident to, adjacent portions of the field of view, thereby selectively adjusting the optical attenuation of the one or more portions of the field of view.

10. The optical system according to claim 9, wherein the optical attenuation module is arranged in a light path between an illumination source of the optical system and the object, or wherein the optical attenuation module is arranged in a light path between a user of the optical system and the object.

11. The optical system according to claim 1, wherein the processing module is configured to selectively adjust the illumination of the one or more portions of the field of view, or the optical attenuation of the one of more portions of the field of view, in order to achieve at least a pre-defined contrast between the visual overlay and the object.

12. The optical system according to claim 1, wherein the object is a sample of organic tissue, wherein the visual overlay is configured to highlight one or more portions of the sample of organic tissue.

13. An apparatus for an optical system, the apparatus comprising:
an interface for communicating with one or more components of the optical system; and
a processing module connected to the interface, the processing module configured to:
determine at least one optical property of an object using at least one sensor of the optical system,
determine a visual contrast, as perceived within a field of view of an augmented reality or mixed reality environment, between a visual overlay to be overlaid over the object in the augmented reality or mixed reality environment and the object, based on the at least one optical property of the object, and
selectively adjust an illumination of one of more portions of the field of view, or an optical attenuation of the one of more portions of the field of view, based on the determined visual contrast between the visual overlay to be overlaid over the object and the object.

14. A method for an optical system, the method comprising:
determining at least one optical property of an object using at least one sensor of the optical system, and
determining a visual contrast, as perceived within a field of view of an augmented reality or mixed reality environment, between a visual overlay to be overlaid over the object in the augmented reality or mixed reality environment and the object, based on the at least one optical property of the object, and
selectively adjusting an illumination of one of more portions of the field of view, or an optical attenuation of the one of more portions of the field of view, based on the determined visual contrast between the visual overlay to be overlaid over the object and the object.

15. A non-transitory computer-readable medium storing a computer program comprising instructions which, when the instructions are executed by a processor, cause the processor to perform the method according to claim 14.

\* \* \* \* \*